United States Patent [19]

Sauvaire et al.

[11] Patent Number: 5,470,879
[45] Date of Patent: Nov. 28, 1995

[54] TREATMENT OF NON-INSULIN-DEPENDENT DIABETES

[75] Inventors: Yves Sauvaire, Montferrier sur Lez; Gerard Ribes, Montpellier, both of France

[73] Assignee: Laboratories Monal, France

[21] Appl. No.: 364,079

[22] Filed: Dec. 23, 1994

Related U.S. Application Data

[62] Division of Ser. No. 113,951, Aug. 31, 1993, abandoned.

[30] Foreign Application Priority Data

Sep. 7, 1992 [FR] France .................................. 92 10644

[51] Int. Cl.⁶ ...................................................... A61K 35/78
[52] U.S. Cl. ............................................................. 514/561
[58] Field of Search ................................................ 514/561

[56] References Cited

U.S. PATENT DOCUMENTS 5,132,113  7/1992  Lucá ..................... 424/195.1

OTHER PUBLICATIONS

Chemical Abstracts, CA79(15):89492p, 1973, Fowden et al, "4–Hydroxyisoleucine from seed of Trigonella foenum–graecum", see abstract, Phytochemistry, 12(7), 1707–11.

Chemica Abstracts, vol. 94, No. 039690, issued Jun. 16, 1992, "Aminoacid–containing compositions for 05344863.treating diabetes contain rice protein pepsin hydrolysate egg–protein pepsin", see abstract.

*Primary Examiner*—Marianne M. Cintins
*Assistant Examiner*—Keith MacMillan
*Attorney, Agent, or Firm*—Pollock, Vande Sande & Priddy

[57] ABSTRACT

Antidiabetic composition, characterized in that it contains as active substance, in the free or combined state, at least one mono- or polyhydroxylated amino acid and/or its lactone forms and its amidated derivatives.

5 Claims, 5 Drawing Sheets

TREATMENT OF NON-INSULIN-DEPENDENT DIABETES

This application is a division of Ser. No. 08/113,951, filed on Aug. 31, 1993, now abandoned.

FIELD OF THE INVENTION

The present invention relates to an antidiabetic composition intended especially for the treatment of type II diabetes or non-insulin-dependent diabetes.

BACKGROUND OF THE INVENTION

Diabetes is known to affect more than thirty million individuals worldwide at the present time, assuming the dimension of a major phenomenon from the public health standpoint: as an example, it is considered that diabetes affects between 2 and 5% of the population in the countries of Europe, and that approximately 3 to 4% of inhabitants in France suffer from non-insulin-dependent diabetes, which is by far the most frequent, and in particular between 5 and 10% of subjects from 60 to 70 years of age suffer from this disorder.

Furthermore, and for various reasons linked, in particular, to richness of the diet, obesity, smoking or decrease in physical activity, the number of diabetic patients appears to have doubled in France in around twenty years, essentially as a result of an increase in non-insulin-dependent diabetes.

This disorder is characterized by a defect of regulation of insulin secretion, associated or otherwise with an insulin resistance of the peripheral tissues. Impairment of the functioning of the pancreatic B cells which synthesize insulin occurs right from the initial phase of non-insulin-dependent diabetes. It manifests itself in a very marked decrease in insulin secretion in response to a glucose stimulation.

To treat this disorder, the specialists have consequently been led quite naturally to look for products capable of stimulating insulin secretion; among these, only sulfonamides (sulfonylureas) have evinced efficacy: they are consequently the only medicinal products of this type which are currently offered on the market.

SUMMARY OF THE INVENTION

Despite their advantages, sulfonylureas posses a number of drawbacks linked, above all, to the difficulties encountered in determining the appropriate dosage; this results in risks of overdosage which can frequently cause hypoglycaemia, with a risk of hypoglycaemic coma, in particular in elderly individuals.

It would consequently be desirable to be able to have available a medicinal product that can act as a substitute for sulfonylureas for stimulating insulin secretion while not possessing the abovementioned drawbacks.

This was the objective which was set according to the invention.

DETAILED DESCRIPTION OF THE INVENTION

Figure 1:
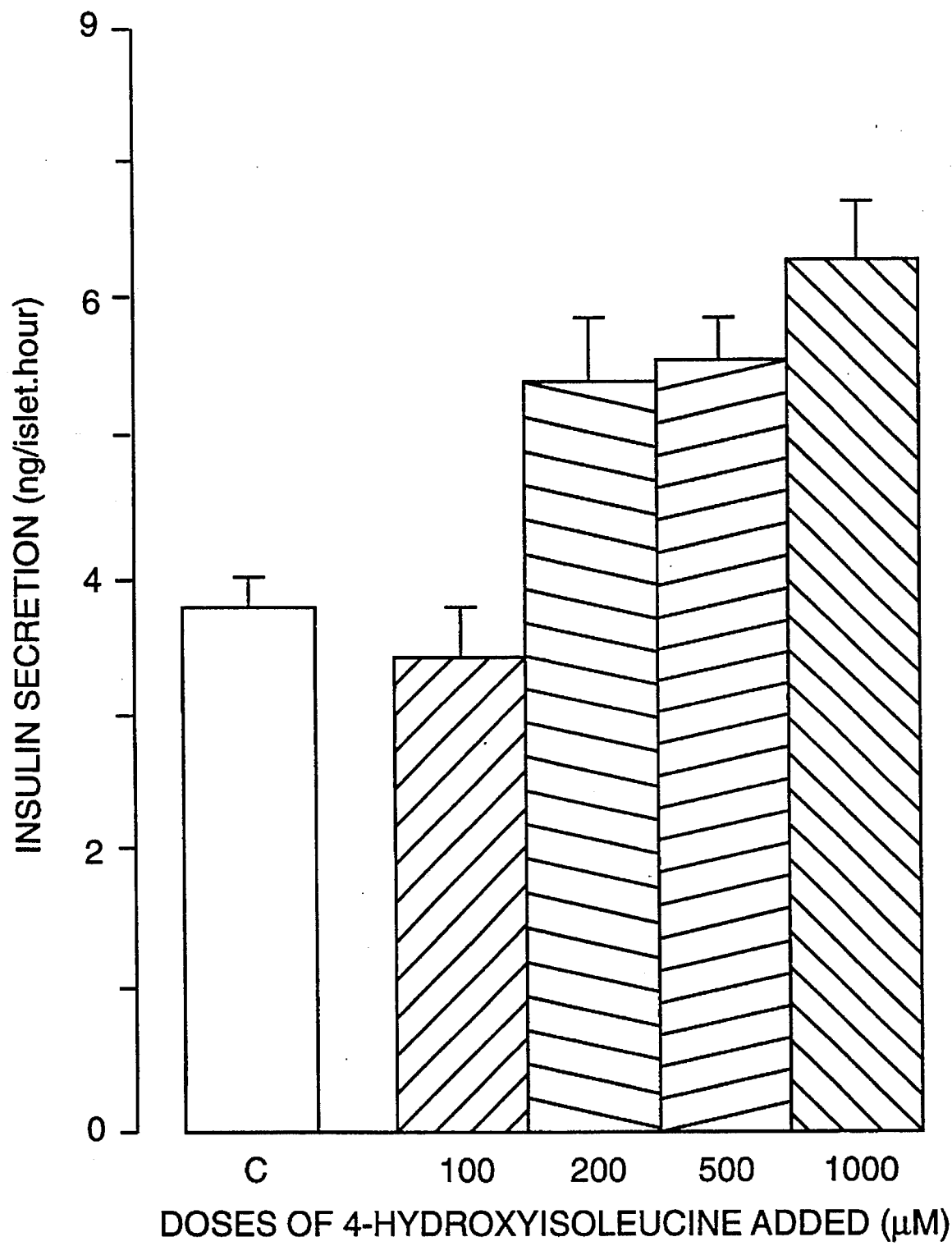
FIG. 1 represents a graph showing an evaluation of the direct effect of a 4-hydroxyisoleucine on the insulin secretion of isolated islets of Langerhans.

To achieve the above objective, it was recalled that it was recommended in antiquity to treat diabetes with decoctions of seeds of a particular species of trigonella which appeared already in Greek and Latin pharmacopeias: fenugreek, *Trigonella foenum-graecum L.*, a legume which can be readily cultivated in the Mediterranean regions.

The idea of verifying the activity of this plant, and of analyzing the latter by very extensive fractionations with the aim of looking for possible constituents which might be responsible for this activity, thus presented itself.

In this way, it came about that the antidiabetic properties of certain amino acid derivatives were brought to light.

The invention hence relates to an antidiabetic composition containing such derivatives.

This antidiabetic composition is characterized in that it contains as active substance, in the free or combined state, at least one mono- or polyhydroxylated amino acid and/or its lactone forms and its amidated derivatives.

According to another feature of the invention, the composition contains a product originating from the metabolizing of the active substance.

Among the abovementioned amino acids, the most active has proved to be 4-hydroxyisoleucine of formula:

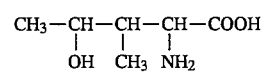

and/or its lactone form and its amidated derivatives.

Consequently, the antidiabetic composition according to the invention preferably contains this compound.

This composition may be administered orally, intravenously or intramuscularly, and contains excipients which are chosen in accordance with the pharmaceutical dosage form adopted.

The dosage can, for its part also, vary within wide limits without thereby departing from the scope of the invention, and depends, in fact, on each particular case to be treated.

The active substance can, naturally, without departing from the scope of the invention, be of any origin, and may, in particular, be obtained synthetically. However, and for reasons of both a philosophical and ecological nature, the specialists are seeking increasingly to offer so-called "natural" products, and the composition according to the invention is advantageously derived from the plant kingdom.

To this end, it has been possible to establish that trigonellae, i.e. *Trigonella sp.* contain not insignificant, usable amounts of hydroxylated amino acids according to the invention possessing antidiabetic activity, and in particular that fenugreek seeds contain considerable amounts of 4-hydroxyisoleucine.

The invention relates especially to a composition endowed with insulin-stimulating properties, capable of being used as a reagent for functional exploration of the endocrine pancreas.

A process for obtaining 4-hydroxyisoleucine from fenugreek seeds will be described below in Example 1:

Example 1

Fenugreek seeds are gathered and subjected to grinding and to a preliminary extraction with hexane at room temperature so as to obtain 100 grams of delipidized cake.

This cake is then subjected to six successive aqueous-alcoholic extractions with 70% ethanol at room temperature (total volume: 2100 ml).

The extract obtained is then concentrated to 130 ml under reduced pressure, and the concentrate is passed through a cation exchange resin in $H^+$ form (AMBERLITE IR 120 or DOWEX 50WX8) in a column 36 cm in height and 2 cm in diameter, so as to retain the desired product on this column. The product is then eluted using N or 2N ammonia solution.

After concentration and taking up with 70% ethanol, the mixture is subjected to adsorption chromatography on a column 50 cm in height and 2.5 cm in diameter packed with 70–230 mesh silica gel 60. 4-hydroxyisoleucine is thereby separated, and is eluted with 70% ethanol (250 ml).

The product is then concentrated under vacuum and purified by crystallization with the addition of diethyl ether.

In this way, it was possible to obtain 0.6 g of 4-hydroxyisoleucine of formula:

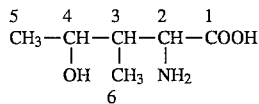

assaying at 99% purity, which was identified and characterized in the manner described below:

Thin-layer chromatography (TLC)

An aqueous-alcoholic (70% ethanol, 30% water) solution of 4-hydroxyisoleucine having a concentration of 4 mg·ml$^{-1}$ is spotted on a plate coated with silica gel G, which is subjected to elution with an n-butanol/CH$_3$COOH/H$_2$O (3:2:1) or phenol/water (3:1) mixture. The plate is then heated to 110° C. for 10 minutes and sprayed with a 0.1% acetone solution of ninhydrin.

4-Hydroxyisoleucine gives a single orange-red to violet spot with both solvent systems. The Rf values are, respectively, as follows:

Rf (n-Butanol/CH$_3$COOH/H$_2$O): 0.36
Rf (Phenol/H$_2$O): 0.45

NMR spectroscopy (VARIAN EM 390 apparatus

This analysis was performed at 90 MHz, using a solution of 4-hydroxyisoleucine in D$_2$O, and TSS (trimethylsilylpropanesulfonic acid Na salt) as internal standard.

Resonances were observed for the following values:

0.95 and 1.25 ppm.

These doublets can be assigned, respectively, to the protons of the CH$_3$ groups of the C-6 and C-5 carbons.

1.85 ppm.

This multiplet can be assigned to the proton of C-3.

3.85 ppm.

This multiplet is composed of a doublet due to the proton of the C-2 carbon and a multiplet due to the proton of the C-4 carbon.

Electron impact mass spectrometry

This analysis was carried out on a JEOL JMS D 100 apparatus at 75 eV.

The following fragmentations were obtained:

148[M+H]$^+$: 5%, 102[M+H–CO$_2$H$_2$]$^+$: 32% 74[M+H–74]$^+$: 92%, 58[M+H–74–16]$^+$: 100%

Fast atom bombardment mass spectroscopy or FAB method

This is a recent technique which entails a more gentle ionization. It is, as a result, much better suited to the characterization of labile polar compounds.

The FAB method is based on the principle of production of ions characteristic of the structure of the test compound by bombardment of the latter with a beam of fast atoms.

The mass spectrum obtained by this ionization method contains:

the quasimolecular ion [M+H]$^+$ present at m/z 148:100% the loss of a molecule of water is demonstrated by the fragmentation m/z 130:35% the loss of CO$_2$H$_2$ from m/z 148 is reflected in the formation of the ion m/z 102:30% the ion m/z 74:56% corresponds to the breaking of the [M+H]$^+$ ion into two fragments (ion and neutral).

In order to establish that these three fragmentations do indeed take place from the m/z 148 [M+H]$^+$ ion, the latter is subjected to a further collision according to the FAB/MS/MS technique. The composition of the ions formed does indeed correspond to the relationship of the products which is demonstrated above.

The abovementioned analyses enable the identity and purity of the 4-hydroxyisoleucine obtained to be clearly demonstrated; it was consequently possible to use this compound for carrying out pharmacological tests enabling the antidiabetic activity of 4-hydroxyisoleucine to be verified; these tests, which were performed, respectively, in vitro on cells and organs and in vivo in animals, are summarized in Examples 2, 3, 4, 5 and 6.

In these examples, the pancreatic hormones (insulin and glucagon) were evaluated by radioimmunoassays.

Blood sugar level was assayed using a Technicon autoanalyzer by the potassium ferricyanide method.

The results were subjected to a variance analysis followed by the multiple comparison test.

Example 2

Investigation on isolated islets of Langerhans of rat pancreas

After digestion of the pancreas with collagenase, the islets of Langerhans, which possess B cells secreting insulin, were separated from the other components of the digest, withdrawn under a dissecting microscope and then placed in incubation tubes. This method, which has the advantage of necessitating only a small amount of substance, permits a direct study of the effects of the composition on pancreatic endocrine cells, especially insulin-secreting B cells, to the exclusion of any interference with the exocrine and related tissues.

The effect of different concentrations of 4-hydroxyisoleucine on insulin secretion was investigated on isolated islets of Wistar rats, incubated in the presence of 8.3 mM glucose (1.5 g/l) for 1 hour. The results obtained are recorded in FIG. 1, in which the histograms represent the insulin secretion measured over 60 minutes for each dose of 4-hydroxyisoleucine.

In this diagram, it may be noted that a stimulatory effect on the secretion is apparent with a 4-hydroxyisoleucine concentration of 200 µM (with an uncertainty of less than 5%). This stimulation of the secretion increases slightly with the dose of 4-hydroxyisoleucine.

By way of comparison, the effects of two structural analogues of 4-hydroxyisoleucine, i.e. isoleucine and leucine, were observed under the same conditions, and it could be established that, with these two substances, the stimulatory effect on insulin secretion is apparent only with concentrations 50 to 100 times as high.

Example 3

Investigation on isolated and perfused rat pancreas

To carry out this test, the pancreas was completely isolated from all the other neighbouring organs and tissues (spleen, stomach, duodenum, epiploic fat) and perfused in an open circuit with a physiological solution in a perfusion chamber. This preparation has the advantage of preserving the functional and vascular integrity of the organ while depriving it of the regulatory influences (humoral or nervous) to which it is normally subjected.

Figure 2:
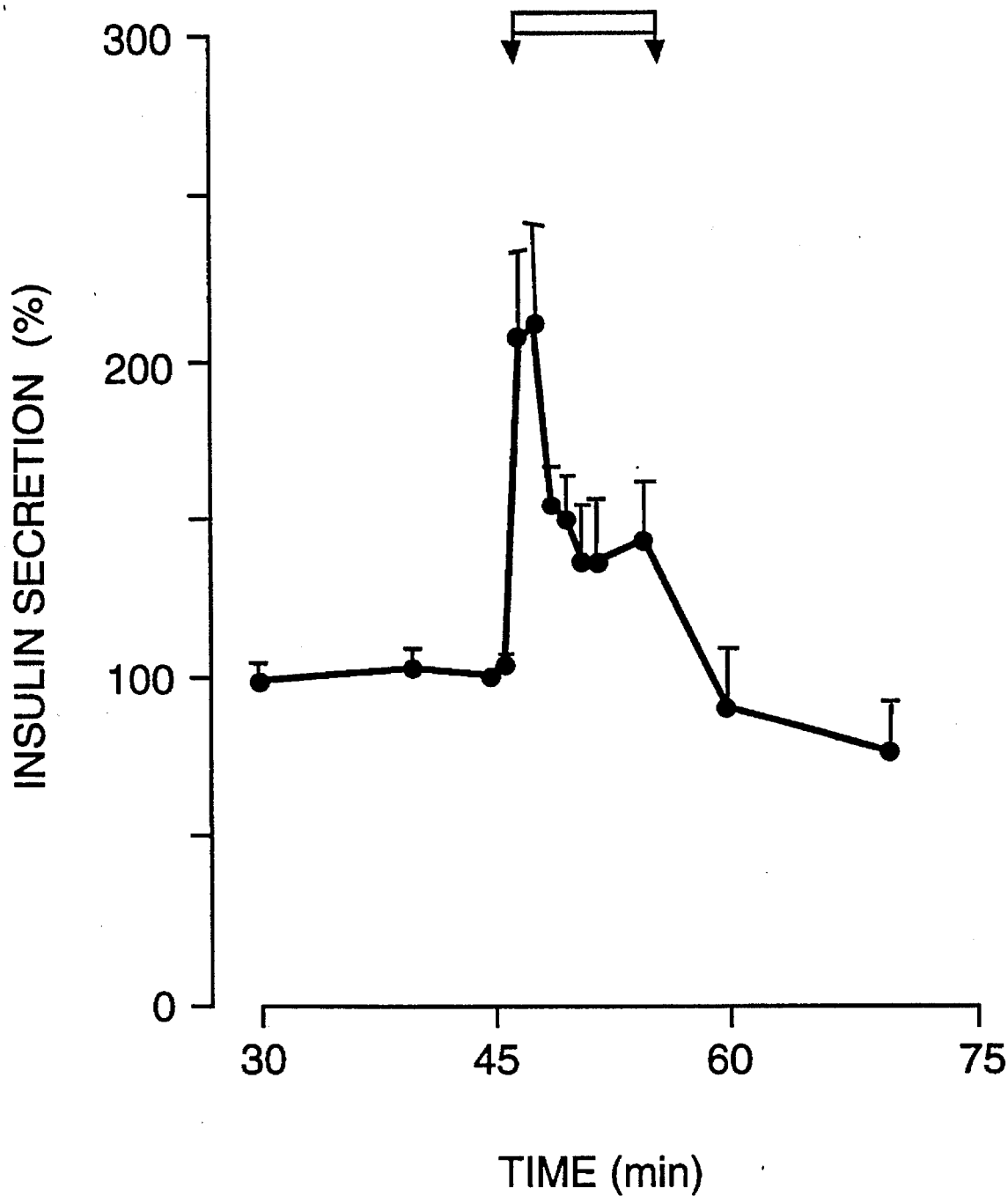
FIG. 2 represents a graph showing the effect on the insulin secretion of an isolated rat pancreas of a perfusion of 4-hydroxyisoleucine at a concentration of 20 μM for 10 minutes.

In this example, the experiments were carried out in the presence of an 8.3 mM concentration of glucose. Under these conditions, the effect on insulin secretion of a perfusion of 4-hydroxyisoleucine at a concentration of 200 µM for 10 minutes was studied. FIG. 2, in which the results of this experiment are recorded, shows clearly that stimulation is immediate and in two phases, and persists throughout the period of the perfusion. The perfusion of the 4-hydroxyisoleucine is indicated by the rectangular box with the lines extending downwardly from opposite sides of the box, near the top of the Figure.

In order to "refine" these results, the effect on insulin secretion of 4-hydroxyisoleucine at concentrations of 50 and 500 µM was also studied. The amounts of insulin secreted during the 10 minutes of perfusion are shown below:

|  | Insulin secretion (ng/10 min) |
| --- | --- |
| Glucose alone | 810 ± 83 |
| Glucose + 4-hydroxyisoleucine (50 µM) | 1232 ± 93 |
| Glucose + 4-hydroxyisoleucine (200 µM) | 1520 ± 154 |
| Glucose + 4-hydroxyisoleucine (500 µM) | 2206 ± 213 |

This table shows that the stimulatory effect increases with the 4-hydroxyisoleucine concentration.

It should be noted that, during these experiments, no modification was observed of pancreatic vascular flow or of the level of pancreatic glucagon, the contra-regulatory hormone which tends in vivo to increase the blood sugar level and consequently to attenuate the effects of stimulation of insulin secretion.

The results show clearly that the stimulation of insulin secretion observed in the presence of the composition is due to a direct stimulation of the B cell of the islet of Langerhans.

Example 4

"In vivo" experiment in rats

During this experiment, Wistar rats were anaesthetized and then provided with catheters in both jugular veins. One catheter enables blood samples needed for the assay of plasma glucose and plasma insulin to be taken, the other catheter is used for the intravenous injection of the test substance.

The attached table in Appendix 1 shows, in anaesthetized Wistar rats previously fed ad libitum, the effect of an acute intravenous administration of 4-hydroxyisoleucine at a dose of 9 mg/kg of body weight on plasma insulin on the one hand and blood sugar level on the other hand.

This table shows that administration of 4-hydroxyisoleucine triggers an immediate and particularly important increase in the plasma insulin level. The consequence of this hyperinsulinaemia is a decrease in blood sugar level. This reduction in the circulating glucose level becomes significant 15 minutes after the injection, and reaches approximately 30% relative to the starting value at the 90th minute.

Under these experimental conditions, no side effect secondary to the injection of 4-hydroxyleucine was observed: neither polypnea nor tachycardia nor hypoxia.

Still in anaesthetized normal rats previously fed ad libitum, an intravenous glucose tolerance test was carried out.

Figure 3:
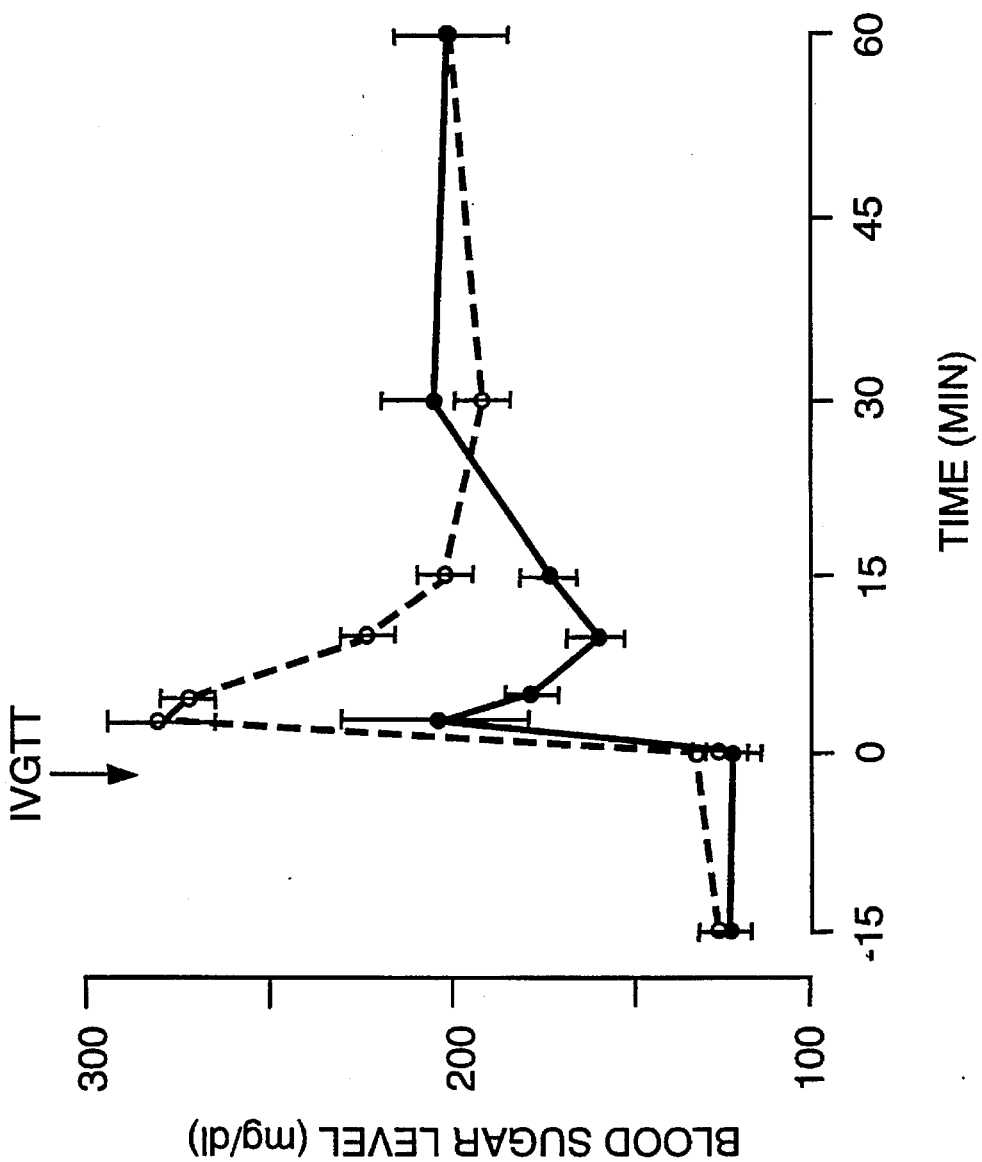
FIG. 3 represents a graph showing the effect of 4-hydroxyisoleucine (9 mg/kg I.V.) on intravenously induced hyperglycemia (IVGTT) produced in anaesthetized normal rats previously fed ad libitum.

Dissolved glucose was administered intravenously at a dose of 0.3 g/kg in one of the two jugular veins of the rat. FIG. 3 shows that the blood sugar level rises immediately and peaks from the 3rd minute at a mean value of 282 mg/dl (i.e. +112%). When 4-hydroxyisoleucine (9 mg/kg) is injected intravenously at the same time as glucose, the hyperglycaemia induced is markedly reduced; the blood sugar level at the 3rd minute reaches only 204 mg/dl (i.e. +58%). In FIG. 3, "o" indicates the values observed when administering glucose alone, while "•" indicates the values observed during the administration of glucose plus 4-hydroxyisoleucine.

Example 5

"In vivo" experiment in dogs

During a complementary experiment in dogs, we investigated whether 4-hydroxyisoleucine can be active after oral administration, and whether, in this case, this substance retains its insulin-secreting property and consequently its capacity to improve glucose tolerance.

Using conscious normal dogs kept fasted for 18 hours, 4-hydroxyisoleucine is dissolved in physiological saline and administered by gastric intubation at a dose of 9 mg/kg.

Figure 4A:
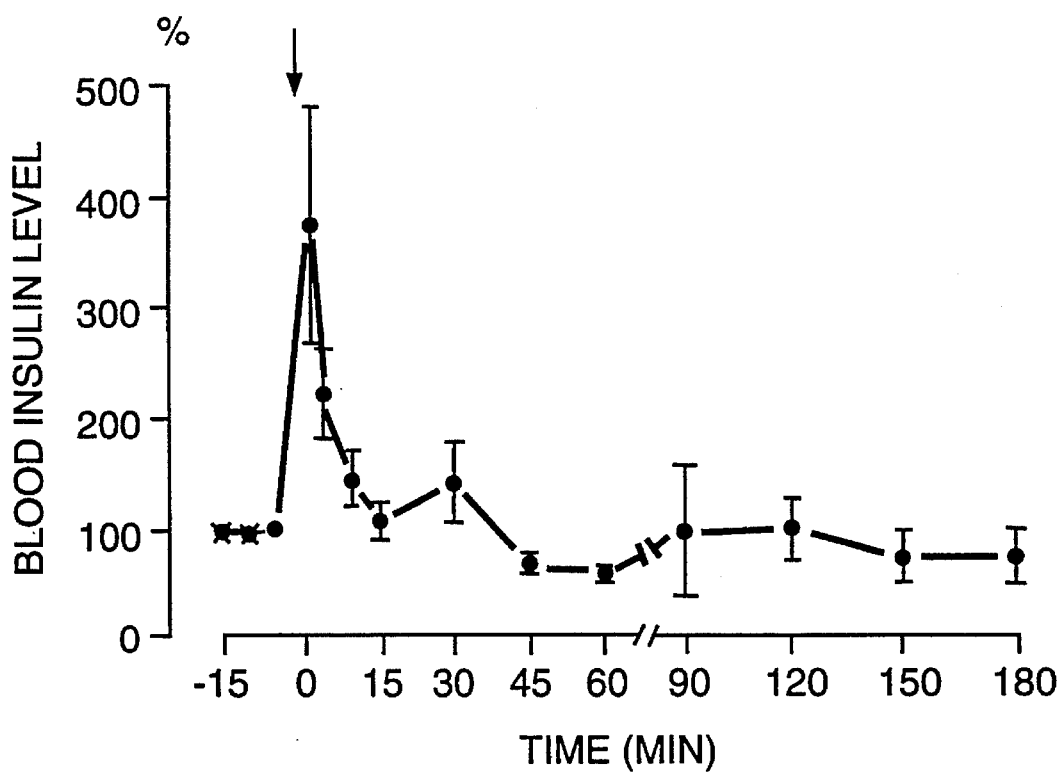
FIG. 4A and FIG. 4B represent graphs showing the effects on insulin and blood sugar levels, respectively, of an administration of 4-hydroxyisoleucine (9 mg/kg) by gastric intubation in fasted conscious normal dogs.
Figure 4B:
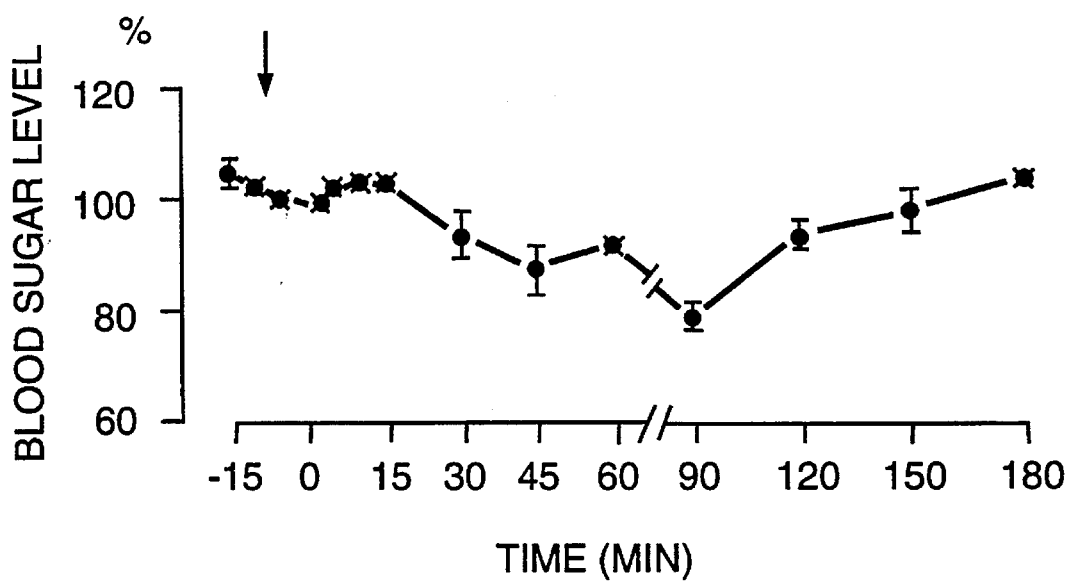

Blood samples drawn from one of the two jugular veins enabled the blood insulin and sugar levels of these animals to be evaluated. FIG. 4A shows that 4-hydroxyisoleucine triggers a very rapid and considerable rise in blood insulin level, which reaches +277% from the 3rd minute. This hyperinsulinaemia which, under our conditions of fasting, lasts only 5 minutes, is accompanied by a gradual and discrete reduction in blood sugar level, as shown in FIG. 4B. The arrows near the top of FIGS. 4A and 4B represent the approximate time of administration of the 4-hydroxyisoleucine.

A test of orally induced hyperglycaemia was then carried out under the same conditions in dogs.

Dissolved glucose was administered by gastric intubation at a dose of 1 g/kg.

Example 6

The acute toxicity was determined in Swiss mice of both sexes on intraperitoneal administration of a single dose of 1 gram per kilo of 4-hydroxyisoleucine. Observation of these animals over a period of 15 days following the administration does not appear to detect any toxic phenomenon. The LD$_o$ (zero lethal dose) is greater than 1 gram per kilo under our experimental conditions.

Autopsy carried out at the end of this study does not appear to disclose any macroscopic deleterious effect on the main organs observed: thymus, heart, lungs, liver, stomach, kidneys, adrenals, pancreas, duodenum, genital tract and bladder.

Figure 5:
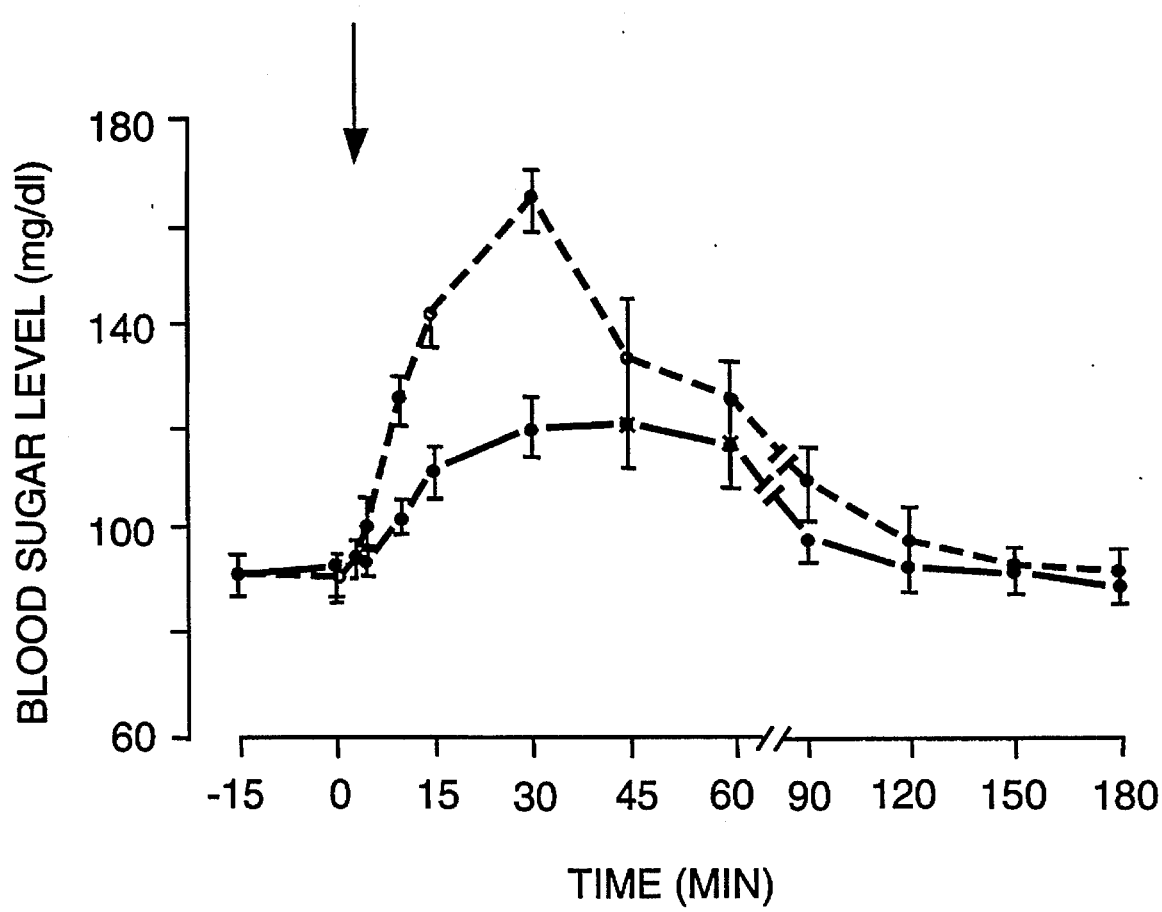
FIG. 5 represents a graph showing the effect of 4-hydroxyisoleucine (9 mg/kg administered intragastrically) on orally induced hyperglycemia (OGTT) produced in fasted conscious normal dogs.

FIG. 5 shows that the blood sugar level, assayed on blood drawn from a jugular vein, rises gradually from the 5th minute and reaches its maximum at the 30th minute (166 mg/dl, i.e. +85%). In FIG. 5, "o" represents values observed upon administering glucose alone; "•" represents values observed in a trial in which glucose plus 4-hydroxyisoleucine is administered. The arrow toward the top of FIG. 5 represents the point of administration of the glucose or glucose plus 4-hydroxyisoleucine. When 4-hydroxyisoleucine (9 mg/kg) is added to the glucose solution administered by gastric intubation, the blood sugar level reaches only 120 mg/dl at the 30th minute, i.e. only +31%.

The abovementioned tests show clearly that 4-hydroxyisoleucine is a substance which has the property of powerfully stimulating insulin secretion at all levels of organization: cellular, isolated organ, whole animal "in vivo", the induction of hyperinsulinaemia has as its consequence a reduction in blood sugar level, irrespective of whether the 4-hydroxyisoleucine is administered intravenously or orally. The "in vitro" tests show that 4-hydroxyisoleucine, at concentrations of the order of 1 µM, stimulates insulin secretion by a direct effect on the B cell of the islet of Langerhans.

It is hence clear that 4-hydroxyisoleucine could be advantageously used as an active product in compositions intended for the therapy of non-insulin-dependent diabetes, both orally and intravenously. This possibility is strengthened by the fact that 4-hydroxyisoleucine improves glucose tolerance intravenously or orally in both animal species studied: rat and dog.

APPENDIX 1

Effect of an intravenous injection of 4-hydroxyisoleucine at a dose of 9 mg/kg of body weight, in anaesthetized Wistar rats fed ad libitum, on plasma insulin and blood sugar level.

| | Minutes | | | | |
|---|---|---|---|---|---|
| | −15 | −10 | −2 | 2 | 5 |
| Plasma insulin (ng/ml) | 2.8 ± 0.2 | 2.4 ± 0.1 | 3.4 ± 1.1 | 4.4 ± 1.1 | 9.1 ± 1.0 |
| Blood sugar level (g/l) | 1.32 ± 0.09 | 1.38 ± 0.09 | 1.34 ± 0.07 | 1.26 ± 0.08 | 1.18 ± 0.04 |

| | Minutes | | | | |
|---|---|---|---|---|---|
| | 15 | 30 | 45 | 60 | 90 |
| Plasma insulin (ng/ml) | 18.5 ± 1.5 | 18.6 ± 1.5 | 14.5 ± 4.8 | 14.4 ± 4.8 | 14.9 ± 5.2 |
| Blood sugar level (g/l) | 0.94 ± 0.09 | 0.99 ± 0.10 | 0.99 ± 0.12 | 0.94 ± 0.10 | 0.89 ± 0.12 |

I.V. composition

We claim:

1. Process for stimulating the secretion of insulin and for the treatment of non-insulin dependent diabetes by the administration of effective quantities of substantially pure 4-hydroxyisoleucine of the formula:

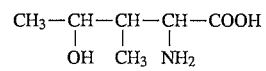

or its lactone form or mixtures thereof.

2. Process according to claim 1 characterized by the administration of 4-hydroxyisoleucine of a vegetable origin.

3. Process according to claim 2 characterized by the administration of 4-hydroxyisoleucine obtained from trigonelles (*Trigonella SP*).

4. Process according to claim 3 characterized by the administration of 4-hydroxyisoleucine extracted from fenugreek grains (*Trigonella foenum graecum L*).

5. Process according to claim 4 characterized by the administration of 4-hydroxyisoleucine obtained by:

A) subjecting fenugreek grains (*Trigonella foenum graecum L*) to a grinding and a preliminary extraction with hexane, at an ambient temperature in such a manner as to obtain a lipid-free cake;

B) subjecting said lipid-free cake to several successive aqueous-alcoholic extractions with ethanol at 70% at an ambient temperature;

C) concentrating the extract obtained from step B under reduced pressure;

D) passing the concentrate from step C over a column containing a cationic exchange resin in H$^+$ form in such a manner as to retain on this column, the desired 4-hydroxyisoleucine;

E) eluting said 4-hydroxyisoleucine using an N or 2N ammonia solution;

F) concentrating and recovering said 4-hydroxyisoleucine using ethanol at 70% to provide a mixture;

G) subjecting said mixture to an adsorption chromatography on silica gel; and

H) eluting with ethanol at 70%, followed by concentrating under vacuum and purifying, by crystallization with the addition to diethyl ether in such a manner as to obtain a 4-hydroxyisoleucine with 99% purity.

\* \* \* \* \*